(12) United States Patent
Kimura (10) Patent No.: US 6,417,924 B1
(45) Date of Patent: Jul. 9, 2002

(54) SURFACE PLASMON SENSOR OBTAINING TOTAL REFLECTION BREAK ANGLE BASED ON DIFFERENCE FROM CRITICAL ANGLE

(75) Inventor: Toshihito Kimura, Kaisei-machi (JP)

(73) Assignee: Fuji Photo Film Co., Ltd., Kanagawa-Ken (JP)

(*) Notice: Subject to any disclaimer, the term of this patent is extended or adjusted under 35 U.S.C. 154(b) by 0 days.

(21) Appl. No.: 09/468,080

(22) Filed: Dec. 21, 1999

(30) Foreign Application Priority Data

Dec. 21, 1998 (JP) .......................... 10-362030

(51) Int. Cl.[7] ............................................. G01N 21/55
(52) U.S. Cl. ..................................................... 356/445
(58) Field of Search ......................................... 356/445

(56) References Cited

U.S. PATENT DOCUMENTS 4,844,613 A * 7/1989 Batchelder et al. ......... 356/445
5,434,663 A * 7/1995 Maule ......................... 356/445
6,208,422 B1 * 3/2001 Naya ........................... 356/445

FOREIGN PATENT DOCUMENTS

JP      6-167443      6/1994      .......... G01N/21/27

* cited by examiner

Primary Examiner—Richard A. Rosenberger
(74) Attorney, Agent, or Firm—Sughrue Mion, PLLC (57) ABSTRACT

A surface plasmon sensor contains a dielectric material forming a prism or the like, and a metal film formed on a face of the dielectric material. A sample to be analyzed is dropped on the metal film and the face of the dielectric material. A light beam is incident on the metal film at a plurality of incident angles. Light detectors detect reflected light corresponding to the plurality of incident angles to measure a total reflection break angle and a critical angle or a Brewster's angle (polarizing angle). An accurate value of the total reflection break angle is obtained based on a difference between the measured total reflection break angle and the measured critical angle or Brewster's angle.

24 Claims, 3 Drawing Sheets

SURFACE PLASMON SENSOR OBTAINING TOTAL REFLECTION BREAK ANGLE BASED ON DIFFERENCE FROM CRITICAL ANGLE

BACKGROUND OF THE INVENTION

1. Field of the Invention

The present invention relates to a surface plasmon sensor which enables quantitative analysis of a specific material in a sample by utilizing generation of a surface plasmon, and in particular, to a surface plasmon sensor whereby a measurement result is not affected by an inclination of the sample.

2. Description of the Related Art

In a metal, free electrons move collectively to produce a compressional wave called a plasma wave. When a plasma wave generated at the surface of the metal is quantized, the plasma wave is regarded as surface plasmons.

The surface plasmons can be produced by exciting a surface of a metal using an optical wave. Conventionally, various surface plasmon sensors are proposed for performing quantitative analysis of a material in a sample by utilizing the excitation by an optical wave. In particular, surface plasmon sensors which use a system called Kretschmann's arrangement are well known. Refer to Japanese Unexamined Patent Publication No. 6(1994)-167443.

The surface plasmon sensors which use the above system basically contain a prism made of a dielectric material, a metal film formed on a face of the prism and in contact with a sample, a light source producing a light beam, an optical system letting the light through the prism and letting the light beam be incident on a boundary surface between the prism and the metal film at various incident angles, and a light detection unit which can detect the intensity of the light beam reflected by the above boundary surface for each incident angle.

The above various incident angles can be realized by deflecting a relatively thin light beam so that the deflected beam is incident on the boundary surface at a desired incident angle. Otherwise, the various incident angles can be realized by letting a relatively thick light beam be incident on the boundary surface so that the thick light beam converges near or at the boundary surface, and therefore the converging beam contains components incident on the boundary surface at the various incident angles. When deflecting the relatively thin light beam, the light beam reflected at a reflection angle which varies with the deflection of the incident light beam can be detected by a small light detector which moves corresponding to the deflection of the incident light beam, or by an area sensor extending in the direction of the variation of the reflection angle. When letting the relatively thick light beam be incident on the boundary surface as above, the reflected light beam can be detected by an area sensor which extends in the direction of the variation of the reflection angle so that substantially all of the reflected light beam can be detected.

When a light beam is incident on the metal film at a specific incident angle $\theta_{SP}$ which is greater than a critical angle for total reflection in the surface plasmon sensor having the above construction, an evanescent wave is generated, where an electric field of the evanescent wave spreads out near the metal film in the sample. As a result of the evanescent wave, surface plasmons are generated at the boundary surface between the metal film and the sample. When the wave number of the evanescent wave equals the wave number of the surface plasmons, i.e., these wave numbers match, the evanescent wave is resonant with the surface plasmons, and the energy of the evanescent wave transfers to the surface plasmons. Therefore, the intensity of the light totally reflected by the boundary surface between the prism and the metal film sharply decreases at the above specific incident angle $\theta_{SP}$.

When the wave number of the surface plasmon is obtained based on the incident angle $\theta_{SP}$ (generally called total reflection break angle) at which the above intensity decreases, the permittivity of the sample can be obtained from the wave number of the surface plasmons. That is, $$K_{SP}(\omega)=(\omega/c)\sqrt{\epsilon_m(\omega)\cdot\epsilon_s/(\epsilon_m(\omega)+\epsilon_s)},$$

where the wave number of the surface plasmon is denoted by $K_{SP}$, the angular frequency of the surface plasmon is denoted by $\omega$, the velocity of light in vacuum is denoted by $c$, and permittivities of the metal and the sample are denoted by $\epsilon_m$ and $\epsilon_s$, respectively.

When the permittivity $\epsilon_s$ of the sample is obtained, the concentration of the specific material in the sample can be obtained based on a predetermined calibration curve or the like. Therefore, a quantitative analysis of the specific material in the sample can be performed by obtaining the incident angle $\theta_{SP}$ at which the intensity of the reflected light decreases.

In the conventional surface plasmon sensors as described above, the sample is analyzed based on a detected value of the total reflection break angle $\theta_{SP}$ per se. Therefore, when the prism (i.e., the sample) tilts away from a predetermined position, such an inclination will produce an error in measurement of the permittivity of the sample, and this error in the permittivity will cause an error in the analysis of the sample.

In addition, a variation in a refractive index of the dielectric material or the metal film, or a deformation of the dielectric material or the metal film will also cause an error in the analysis of the sample.

SUMMARY OF THE INVENTION

An object of the present invention is to provide a surface plasmon sensor which can perform accurate analysis of a sample, even if the sample tilts, the prism or the metal film is deformed, or there is a variation in the refractive index of the prism or the metal film.

According to the first aspect of the present invention, there is provided a surface plasmon sensor which contains a dielectric material forming a prism or the like, a metal film, a light source generating a light beam, an optical system, and a light detecting unit. In the surface plasmon sensor, the light beam is led to the metal film formed on a face of the prism, and is reflected at that point. Provision is made for measuring a critical angle or a Brewster's angle (polarizing angle), and for canceling errors in measurement of the total reflection break angle based on the critical angle or the Brewster's angle.

To put it concretely, the surface plasmon sensor according to the present invention contains a dielectric material, a metal film formed on a face of the dielectric material and in contact with a sample, a first light source for generating a first light beam, a first optical system for letting the first light beam pass through the dielectric material and letting the first light beam be incident on a boundary surface between the dielectric material and the metal film at a first plurality of incident angles, a first light detecting unit which can detect the first light beam totally reflected by the boundary surface corresponding to the first plurality of incident angles, a second light source for generating a second light beam, a second optical system for letting the second light beam pass through the dielectric material and letting the second light beam be incident on the face of the dielectric material at a second plurality of incident angles, a second light detecting unit which can detect the second light beam regularly reflected by the face of the dielectric material corresponding to the second plurality of incident angles, a total reflection break angle obtaining unit for obtaining a total reflection break angle of the first light beam based on a result of detection by the first light detecting unit, and a critical angle obtaining unit for obtaining a critical angle of the second light beam based on a result of detection by the second light detecting unit.

Preferably, the above surface plasmon sensor may further contain a unit for obtaining a difference between the total reflection break angle and the critical angle, so that the difference can be obtained automatically and thus easily.

According to second aspect of the present invention, there is provided a surface plasmon sensor which contains a unit for obtaining the Brewster's angle (polarizing angle) of the second light beam, instead of the critical angle obtaining unit in the first aspect of the present invention.

In the second aspect of the present invention, preferably, the surface plasmon sensor may further contain a unit for obtaining a difference between the total reflection break angle and the Brewster's angle, so that the difference can be obtained automatically and thus easily.

In the first and second aspects of the present invention, preferably, at least light receiving portions of the first and second light detecting units may be realized by a common unit.

In the first and second aspects of the present invention, preferably, the first and second light sources may be realized by a common light source.

In the first and second aspects of the present invention, preferably, the first and second optical systems may be realized by a common optical system.

DESCRIPTION OF THE PREFERRED EMBODIMENTS

The present invention is explained in detail below with reference to the drawings.

Basic Principle

Figure 1:
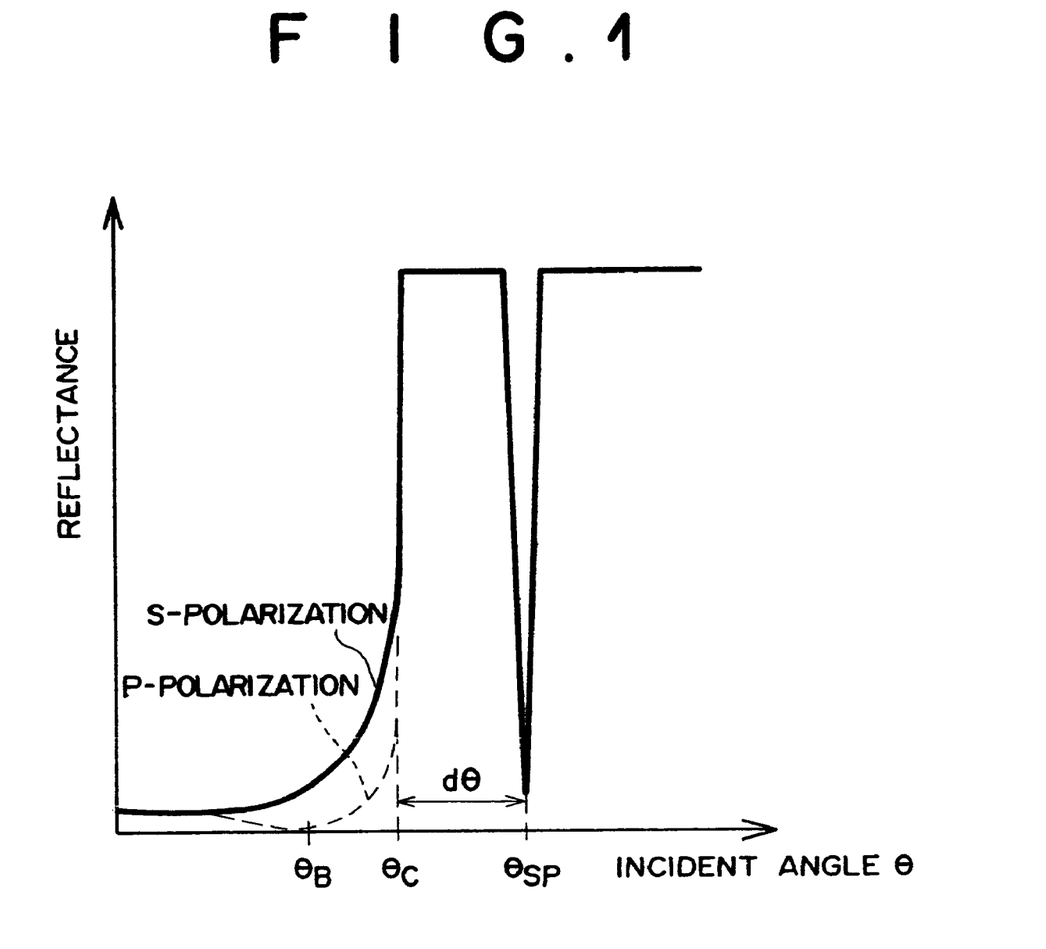
FIG. 1 is a block diagram illustrating a relationship between the reflectance and the incident angle covering the Brewster's angle, the critical angle, and the total reflection break angle in a surface plasmon sensor.

FIG. 1 is a block diagram illustrating a relationship between the reflectance and the incident angle covering the Brewster's angle, the critical angle, and the total reflection break angle in a surface plasmon sensor containing a dielectric material, a metal film formed on a face of the dielectric material and in contact with a sample, a light source generating a light beam, an optical system for letting the light beam pass through the dielectric material and letting the light beam be incident on a boundary surface between the dielectric material and the metal film at a plurality of incident angles, and a light detecting unit which can detect the light beam totally reflected by the boundary surface for each of the plurality of incident angles.

As illustrated in FIG. 1, the total reflection occurs when the incident angle is equal to or greater than the critical angle $\theta_c$. When the incident angle is greater than the critical angle $\theta_c$, the total reflection breaks at the total reflection break angle $\theta_{SP}$ due to the resonance of the surface plasmon. When the incident angle is equal to the Brewster's angle $\theta_B$, the reflectance of the p-polarization (polarization parallel to the plane of incidence) component of the incident light beam is equal to zero.

If the sample tilts away from the horizontal position in which the sample should be placed, the total reflection break angle $\theta_{SP}$ is erroneously measured, and therefore the analysis of the sample cannot be performed accurately. However, when the sample tilts away, the measured values of the total reflection break angle $\theta_{SP}$ and the critical angle $\theta_c$ are changed by the same amount. That is, the difference $\Delta\theta$ (as illustrated in FIG. 1) between the measured values of the total reflection break angle $\theta_{SP}$ and the critical angle $\theta_c$ does not change even if the sample tilts. The total reflection break angle $\theta_{SP}$ is determined by the permittivity of the sample, and the critical angle $\theta_c$ is determined by the refractive indexes of the mediums on both sides of the boundary surface by which the light beam is reflected. Therefore, when the difference $\Delta\theta$ (as illustrated in FIG. 1) between the total reflection break angle $\theta_{SP}$ and the critical angle $\theta_c$ is obtained by the measurement, the accurate value of the total reflection break angle $\theta_{SP}$ can be obtained from the difference $\Delta\theta$ and the critical angle $\theta_c$ which is determined by the refractive indexes of the mediums on both sides of the boundary surface by which the light beam is reflected. Thus, the permittivity of the sample can be accurately determined based on the measurement of the difference $\Delta\theta$ between the total reflection break angle $\theta_{SP}$ and the critical angle $\theta_c$, and the sample can be analyzed accurately.

In the surface plasmon sensor according to the first aspect of the present invention, the critical angle $\theta_c$ can be measured, in addition to the total reflection break angle $\theta_{SP}$. Therefore, the difference $\Delta\theta$ between the measured values of the total reflection break angle $\theta_{SP}$ and the critical angle $\theta_c$ can be obtained, and thus the permittivity of the sample can be accurately determined.

As illustrated in FIG. 1, when the sample tilts, the measured values of the total reflection break angle $\theta_{SP}$ and the Brewster's angle (polarizing angle) $\theta_B$ are also changed by the same amount. That is, the difference between the measured values of the total reflection break angle $\theta_{SP}$ and the Brewster's angle (polarizing angle) $\theta_B$ does not change even if the sample tilts. Therefore, when the difference between the total reflection break angle $\theta_{SP}$ and the Brewster's angle (polarizing angle) $\theta_B$ is obtained by the measurement, the total reflection break angle $\theta_{SP}$ can be obtained from the difference and the Brewster's angle (polarizing angle) $\theta_B$ which is also determined by the refractive indexes of the mediums on both sides of the boundary surface by which the light beam is reflected. Thus, the permittivity of the sample can be also accurately determined based on the measurement of the difference between the total reflection break angle $\theta_{SP}$ and the Brewster's angle (polarizing angle) $\theta_B$, and the sample can be analyzed accurately.

In the surface plasmon sensor according to the second aspect of the present invention, the Brewster's angle (polarizing angle) $\theta_B$ can be measured, in addition to the total reflection break angle $\theta_{SP}$. Therefore, the difference between the measured values of the total reflection break angle $\theta_{SP}$ and the Brewster's angle (polarizing angle) $\theta_B$ can be obtained, and thus the permittivity of the sample can be accurately determined, and the sample can be analyzed accurately.

Further, when the variation in refractive index of the dielectric material or the metal film, or the deformation of the dielectric material or the metal film causes the same change in the measured values of the total reflection break angle $\theta_{SP}$ and the critical angle $\theta_c$, the permittivity of the sample can be accurately determined based on the measurement of the difference $\Delta\theta$ between the total reflection break angle $\theta_{SP}$ and the critical angle $\theta_c$, and the sample can be analyzed accurately.

Similarly, when the variation in refractive index of the dielectric material or the metal film, or the deformation of the dielectric material or the metal film causes the same change in the measured values of the total reflection break angle $\theta_{SP}$ and the critical angle $\theta_c$, the permittivity of the sample can be accurately determined based on the measurement of the difference between the total reflection break angle $\theta_{SP}$ and the Brewster's angle (polarizing angle) $\theta_B$, and the sample can be analyzed accurately.

First Embodiment

Figure 2:
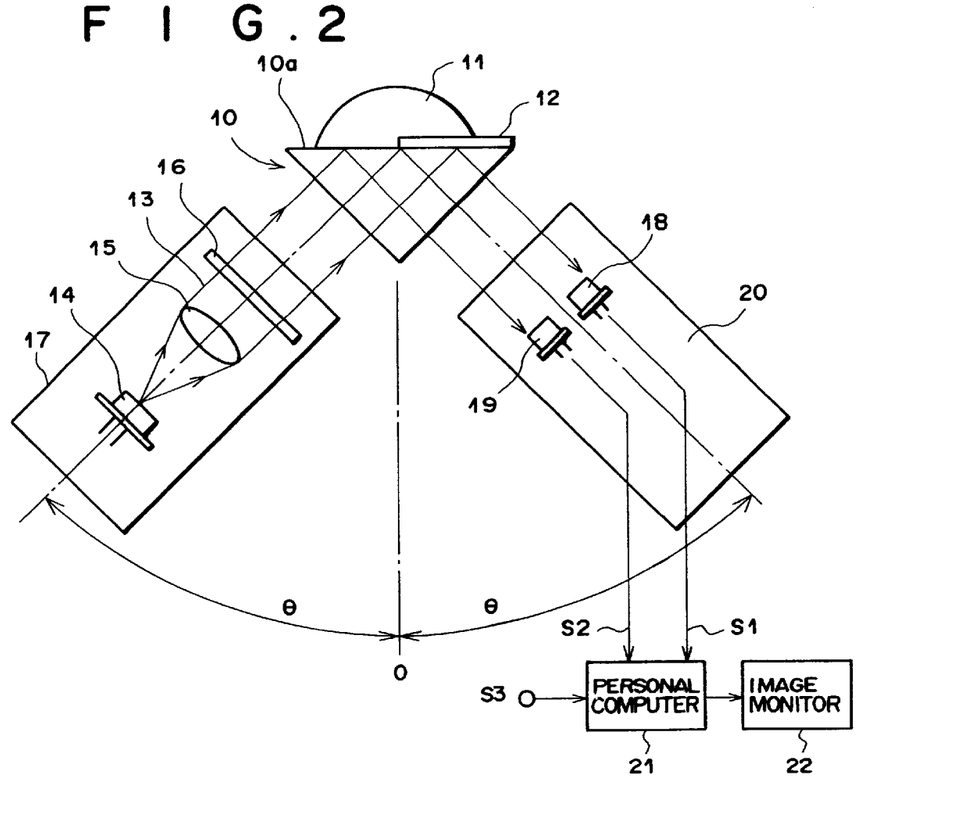
FIG. 2 is a diagram illustrating the construction of the surface plasmon sensor as the first embodiment of the present invention.

FIG. 2 is a diagram (side view) illustrating the construction of the surface plasmon sensor as the first embodiment of the present invention. The surface plasmon sensor of FIG. 1 contains a prism 10, a metal film 12, a light source 14, a collimator lens 15, a polarizing plate 16, and an optical-system swinging table 17.

The prism 10 is made of a dielectric material, and has a triangular. cross-section. The metal film 12 is made of gold, silver, or the like, formed on one face (the upper face 10a in FIG. 2) of the prism 10, and in contact with the sample 11. The light source 14 is realized by a semiconductor laser or the like, which generates a light beam 13. The collimator lens 15 collimates the light beam 13. The polarizing plate 16 is provided in a light path of the collimated light beam to polarize the collimated light beam. The light source 14, the collimator lens 15, and the polarizing plate 16 are mounted on the optical-system swinging table 17.

In addition, the surface plasmon sensor of FIG. 2 contains first and second optical detectors 18 and 19 and an optical detector swinging table 20. The first optical detector 18 receives a light beam reflected by the boundary surface between the prism 10 and the metal film 12, and the second optical detector 19 receives a light beam reflected by the boundary surface between the prism 10 and the sample 11. The first and second optical detectors 18 and 19 are made of, for example, photodiodes, and are mounted on the optical detector swinging table 20, where the optical axes of the first and second optical detectors 18 and 19 are arranged so as to be parallel to the long axis of the optical detector swinging table 20.

The outputs S1 and S2 of the first and second optical detectors 18 and 19 are supplied to the personal computer 21, to which an image monitor 22 such as a CRT display device is connected.

The light source 14 and the polarizing plate 16 are arranged so that substantially only a p-polarization (polarization parallel to the plane of incidence) component of the light beam 13 is incident on the face 10a of the prism 10.

The optical-system swinging table 17 can be swung by a driving unit (not shown) so that an incident angle $\theta$ of the polarized light beam 13 onto the face 10a of the prism 10 varies continuously, where the incident angle $\theta$ is an angle between the normal line O of the face 10a and an optical axis of the collimator lens 15 and the polarizing plate 16. The optical detector swinging table 20, interlocked with the optical-system swinging table 17, swings so that the angle between the long axis of the optical detector swinging table 20 and the above normal line O is always equal to the above incident angle $\theta$. Therefore, the light beam reflected by the boundary surface between the prism 10 and the metal film 12 is normally incident on the first optical detector 18, and the light beam reflected by the boundary surface between the prism 10 and the sample 11 is normally incident on the second optical detector 19.

The operation of the surface plasmon sensor of FIG. 2 is explained below.

The sample 11 to be analyzed is dropped on the face 10a and the metal film 12 so that the sample 11 comes into contact with the metal film 12 as illustrated in FIG. 2. Then, the optical-system swinging table 17 and the optical detector swinging table 20 swing, interlocked with each other. While these tables 17 and 20 are swinging, the outputs S1 and S2 of the first and second optical detectors 18 and 19 are supplied to the personal computer 21.

Figure 3:
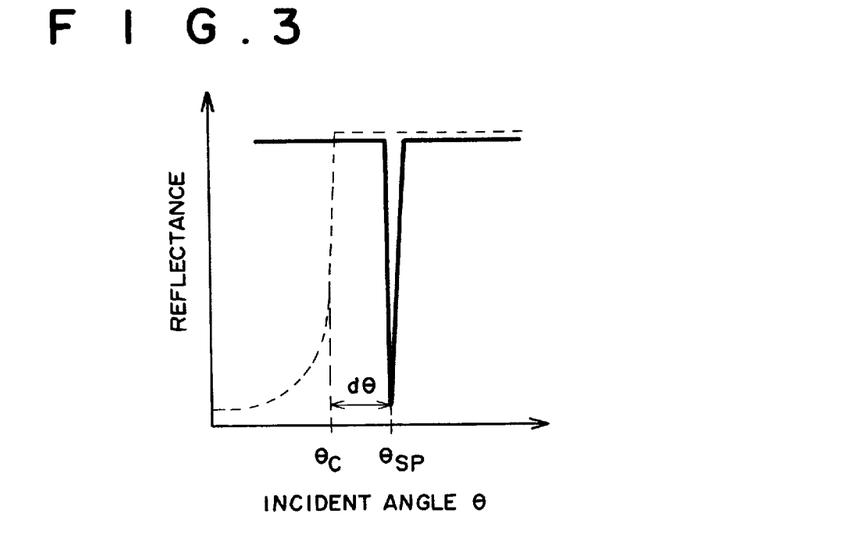
FIG. 3 is a diagram illustrating a relationship between the incident angle θ and the reflectance at the boundary surface between the metal film 12 and the prism 10 (solid curve), and a relationship between the incident angle θ and the reflectance at the boundary surface between the sample 11 and the prism 10 (dashed curve)

The output S1 of the first optical detector 18 indicates the intensity of the light beam reflected by the boundary surface between the metal film 12 and the prism 10, i.e., the reflectance at the boundary surface between the metal film 12 and the prism 10. FIG. 3 shows, by a solid curve, a relationship between the incident angle $\theta$ and the reflectance at the boundary surface between the metal film 12 and the prism 10. The incident angle $\theta$ at each time can be detected, for example, as the swinging angle of the optical-system swinging table 17, and information S3 indicating the detected incident angle is supplied to the personal computer 21.

On the other hand, the output S2 of the second optical detector 19 indicates the intensity of the light beam reflected by the boundary surface between the sample 11 and the prism 10, i.e., the reflectance at the boundary surface between the sample 11 and the prism 10. FIG. 3 shows, by a dashed-line curve, a relationship between the incident angle $\theta$ and the reflectance at the boundary surface between the sample 11 and the prism 10.

The personal computer 21 determines the total reflection break angle $\theta_{SP}$ and the critical angle $\theta_c$ based on the outputs S1 and S2 of the first and second optical detectors 18 and 19 for a series of values of the incident angle $\theta$, and calculates the difference $\Delta\theta$ between the total reflection break angle $\theta_{SP}$ and the critical angle $\theta_c$. The calculated result is then displayed on the image monitor 22.

As explained before, according to the present invention, the total reflection break angle $\theta_{SP}$ is obtained based on the above difference $\Delta\theta$ between the measured values of the total reflection break angle $\theta_{SP}$ and the critical angle $\theta_c$, so that the obtained total reflection break angle $\theta_{SP}$ is not affected by the inclination of the sample 11, or other causes which change the measured values of the total reflection break angle $\theta_{SP}$ and the critical angle $\theta_c$ by the same amount. Thus, the permittivity of the sample 11 can be obtained from the accurate total reflection break angle $\theta_{SP}$, and quantitative analysis of a specific material can be performed based on the accurately obtained permittivity.

In the embodiment of FIG. 2, in order to simplify the construction, the aforementioned first and second light sources in the first aspect of the present invention are realized by the common light source 14, and the first and second optical systems in the first aspect of the present invention are realized by the common collimator lens 15 and the common polarizing plate 16. However, separate optical systems may be provided for measurement of the total reflection break angle $\theta_{SP}$ and the critical angle $\theta_c$, respectively.

Second Embodiment

Figure 4:
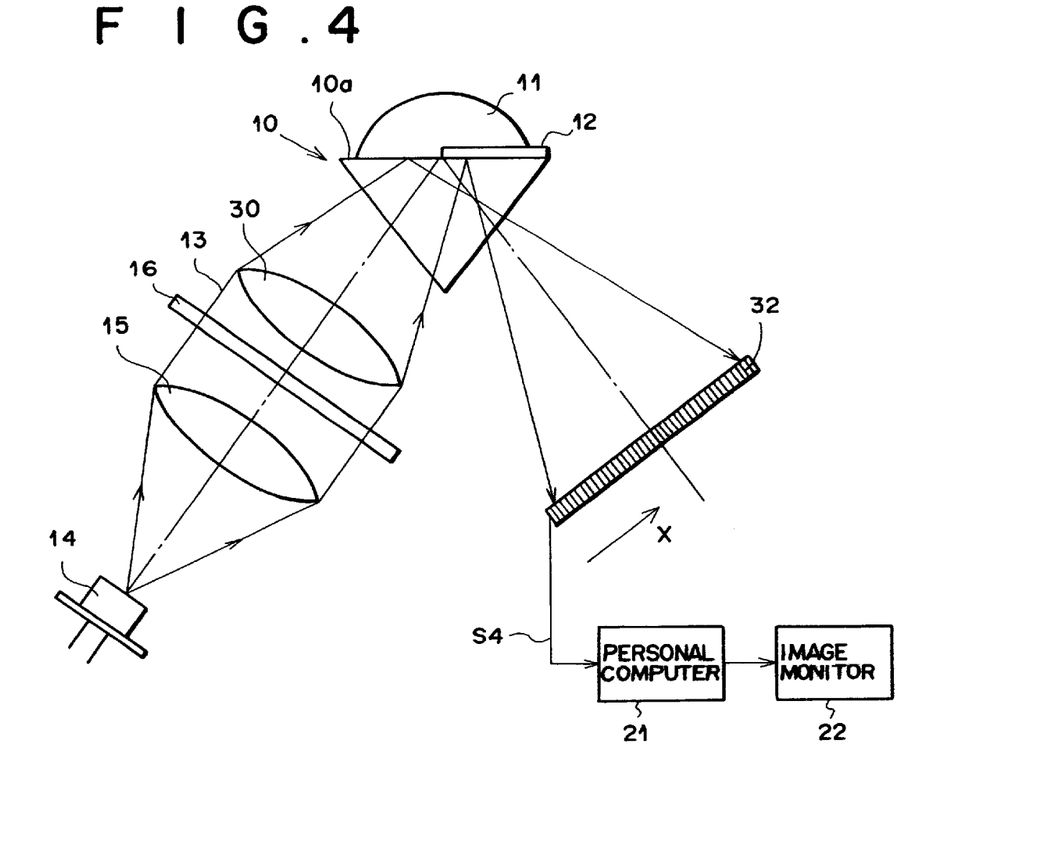
FIG. 4 is a diagram illustrating the construction of the surface plasmon sensor as the second embodiment of the present invention.

FIG. 4 is a diagram illustrating the construction of the surface plasmon sensor as the second embodiment of the present invention. In FIG. 4, the same elements as the elements in the construction of FIG. 2 are denoted by the same reference numerals.

In the construction of FIG. 4, the collimated light beam 13 is further passed through the condenser lens 30 so that the light beam converges until the light beam is incident on the face 10a of the prism 10. Thus, the light beam has a plurality of components incident on the face 10a of the prism 10 at various incident angles.

The light beam 13 reflected by the boundary surface between the prism 10 and the sample 11 or the metal film 12 once converges, and then diverges to be detected by a plurality of light receiving portions of a light detector 32. The plurality of light receiving portions of the light detector 32 are arrayed in the direction (the x-direction indicated in FIG. 4) in which the reflection angle of the light beam varies. That is, the reflected light beam contains a plurality of components which have been reflected at various reflection angles respectively corresponding to the various incident angles. Thus, these components are detected by the respective receiving portions of the optical detector 32. For example, the optical detector 32 may be preferably realized by a photodiode array or a charge-coupled device (CCD).

Figure 5:
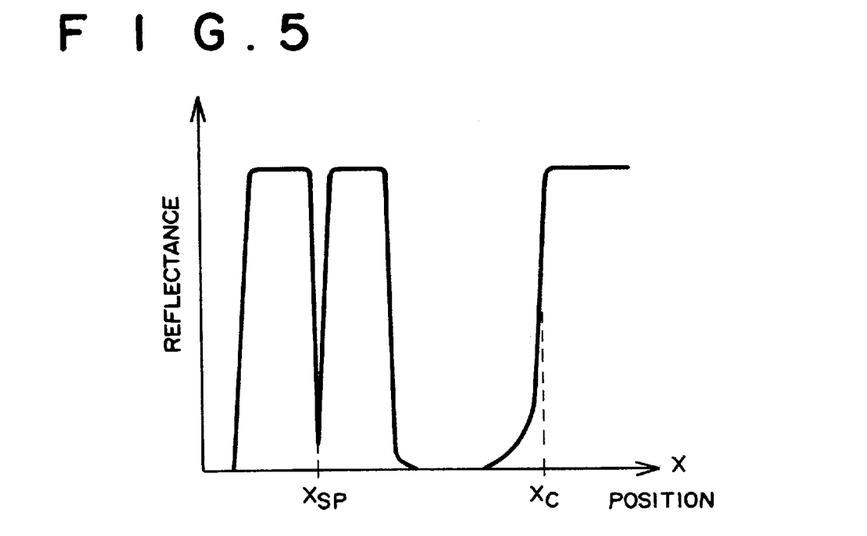
FIG. 5 is a diagram illustrating a relationship between the reflectance and the position of the light detector 32 in the surface plasmon sensor of FIG. 4.

The output S4 of the optical detector 32 is input into the personal computer 21, and indicates intensities (reflectances) of the above plurality of components which have been reflected at various reflection angles by the boundary surface between the prism 10 and the sample 11 and the boundary surface between the prism 10 and the metal film 12, as the outputs of the respective light receiving portions of the light detector 32. An example output of the light detector 32 is illustrated in FIG. 5. Since the respective light receiving portions of the light detector 32 correspond to the incident angles $\theta$, the incident angle $\theta$ can be recognized by the positions of the light receiving portions, as illustrated in FIG. 5. In FIG. 5, the x-coordinate indicates the position of each light receiving portion, the position $x_{SP}$ corresponds to the total reflection break angle $\theta_{SP}$, and the position $x_c$ corresponds to the critical angle $\theta_c$.

The personal computer 21 determines the total reflection break angle $\theta_{SP}$ and the critical angle $\theta_c$ based on the output S4 of the optical detector 32, and calculates the difference $\Delta\theta$ between the total reflection break angle $\theta_{SP}$ and the critical angle $\theta_c$. The calculated result is then displayed on the image monitor 22.

Thus, in a similar manner to the first embodiment, the total reflection break angle $\theta_{SP}$ is obtained based on the above difference $\Delta\theta$ between the measured values of the total reflection break angle $\theta_{SP}$ and the critical angle $\theta_c$, so that the obtained total reflection break angle $\theta_{SP}$ is not affected by the inclination of the sample 11, or other causes which change the detected values of the total reflection break angle $\theta_{SP}$ and the critical angle $\theta_c$ by the same amount. Thus, the permittivity of the sample 11 can be obtained from the accurate total reflection break angle $\theta_{SP}$, and quantitative analysis of a specific material can be performed based on the accurate permittivity.

In the first and second embodiment of FIGS. 2 and 4, the difference between the total reflection break angle $\theta_{SP}$ and the critical angle $\theta_c$ is obtained by automatically calculating them using the personal computer 21. However, the automatic calculation may be dispensed with, and the obtained total reflection break angle $\theta_{SP}$ and critical angle $\theta_c$ may be simply displayed by the image monitor 22 for manual calculation of the difference.

In addition, the above personal computer may store a program for automatically performing the analysis of the sample based on the above difference.

Further, in the above first and second embodiments, the light beam incident on the boundary surface is a p-polarized light beam. Therefore, it is possible to obtain the Brewster's angle (polarizing angle) $\theta_B$ from the outputs of the optical detector(s). Thus, the permittivity of the sample 11 can be obtained from a difference between the total reflection break angle $\theta_{SP}$ and the Brewster's angle (polarizing angle) $\theta_B$, instead of the difference $\Delta\theta$ between the total reflection break angle $\theta_{SP}$ and the critical angle $\theta_c$, and quantitative analysis of a specific material can be performed based on the permittivity. In this case, the obtained total reflection break angle $\theta_{SP}$ is also not affected by the inclination of the sample 11, or other causes which change the detected values of the total reflection break angle $\theta_{SP}$ and the critical angle $\theta_c$ by the same amount.

In addition, all of the contents of the Japanese Patent Application No. 10(1998)-362030 are incorporated into this specification by reference.

What is claimed is:

1. A surface plasmon sensor comprising:
   a dielectric material;
   a metal film formed on a face of the dielectric material and in contact with a sample;
   a first light source for generating a first light beam;
   a first optical system for letting the first light beam pass through the dielectric material and letting the first light beam be incident on a boundary surface between the dielectric material and the metal film at a first plurality of incident angles;
   a first light detecting unit which can detect the first light beam totally reflected by the boundary surface corresponding to the first plurality of incident angles;
   a second light source for generating a second light beam;
   a second optical system for letting the second light beam pass through the dielectric material and letting the second light beam be incident on said face of the dielectric material at a second plurality of incident angles;
   a second light detecting unit which can detect the second light beam regularly reflected by said face corresponding to the second plurality of incident angles;
   a total reflection break angle obtaining unit for obtaining a total reflection break angle of the first light beam based on a result of detection by the first light detecting unit; and a critical angle obtaining unit for obtaining a critical angle of the second light beam based on a result of detection by the second light detecting unit.

2. A surface plasmon sensor according to claim 1, further comprising a unit for obtaining a difference between said total reflection break angle and said critical angle.

3. A surface plasmon sensor comprising:

a dielectric material;

a metal film formed on a face of the dielectric material and in contact with a sample;

a first light source for generating a first light beam;

a first optical system for letting the first light beam pass through the dielectric material and letting the first light beam be incident on a boundary surface between the dielectric material and the metal film at a first plurality of incident angles;

a second light source for generating a second light beam;

a second optical system for letting the second light beam pass through the dielectric material and letting the second light beam be incident on said face of the dielectric material at a second plurality of incident angles;

a light detecting unit which can detect the first light beam totally reflected by the boundary surface corresponding to the first plurality of incident angles, and can detect the second light beam regularly reflected by said face corresponding to the second plurality of incident angles;

a total reflection break angle obtaining unit for obtaining a total reflection break angle of the first light beam based on a result of detection by the light detecting unit; and a critical angle obtaining unit for obtaining a critical angle of the second light beam based on a result of detection by the light detecting unit.

4. A surface plasmon sensor comprising:

a dielectric material;

a metal film formed on a face of the dielectric material and in contact with a sample;

a light source for generating a first light beam and a second light beam;

a first optical system for letting the first light beam pass through the dielectric material and letting the first light beam be incident on a boundary surface between the dielectric material and the metal film at a first plurality of incident angles;

a first light detecting unit which can detect the first light beam totally reflected by the boundary surface corresponding to the first plurality of incident angles;

a second optical system for letting the second light beam pass through the dielectric material and letting the second light beam be incident on said face of the dielectric material at a second plurality of incident angles;

a second light detecting unit which can detect the second light beam regularly reflected by said face corresponding to the second plurality of incident angles;

a total reflection break angle obtaining unit for obtaining a total reflection break angle of the first light beam based on a result of detection by the first light detecting unit; and a critical angle obtaining unit for obtaining a critical angle of the second light beam based on a result of detection by the second light detecting unit.

5. A surface plasmon sensor comprising:

a dielectric material;

a metal film formed on a face of the dielectric material and in contact with a sample;

a first light source for generating a first light beam;

a second light source for generating a second light beam;

an optical system for letting the first light beam pass through the dielectric material and letting the first light beam be incident on a boundary surface between the dielectric material and the metal film at a first plurality of incident angles, and for letting the second light beam pass through the dielectric material and letting the second light beam be incident on said face of the dielectric material at a second plurality of incident angles;

a first light detecting unit which can detect the first light beam totally reflected by the boundary surface corresponding to the first plurality of incident angles;

a second light detecting unit which can detect the second light beam regularly reflected by said face corresponding to the second plurality of incident angles;

a total reflection break angle obtaining unit for obtaining a total reflection break angle of the first light beam based on a result of detection by the first light detecting unit; and a critical angle obtaining unit for obtaining a critical angle of the second light beam based on a result of detection by the second light detecting unit.

6. A surface plasmon sensor comprising:

a dielectric material;

a metal film formed on a face of the dielectric material and in contact with a sample;

a first light source for generating a first light beam;

a first optical system for letting the first light beam pass through the dielectric material and letting the first light beam be incident on a boundary surface between the dielectric material and the metal film at a first plurality of incident angles;

a first light detecting unit which can detect the first light beam totally reflected by the boundary surface corresponding to the first plurality of incident angles;

a second light source for generating a second light beam;

a second optical system for letting the second light beam pass through the dielectric material and letting the second light beam be incident on said face of the dielectric material at a second plurality of incident angles;

a second light detecting unit which can detect the second light beam regularly reflected by said face corresponding to the second plurality of incident angles;

a total reflection break angle obtaining unit for obtaining a total reflection break angle of the first light beam based on a result of detection by the first light detecting unit; and a Brewster's angle obtaining unit for obtaining a Brewster's angle of the second light beam based on a result of detection by the second light detecting unit.

7. A surface plasmon sensor according to claim 6, further comprising a unit for obtaining a difference between said total reflection break angle and said Brewster's angle.

8. A surface plasmon sensor comprising:

a dielectric material;

a metal film formed on a face of the dielectric material and in contact with a sample;

a first light source for generating a first light beam;
a first optical system for letting the first light beam pass through the dielectric material and letting the first light beam be incident on a boundary surface between the dielectric material and the metal film at a first plurality of incident angles;
a second light source for generating a second light beam;
a second optical system for letting the second light beam pass through the dielectric material and letting the second light beam be incident on said face of the dielectric material at a second plurality of incident angles;
a light detecting unit which can detect the first light beam totally reflected by the boundary surface corresponding to the first plurality of incident angles, and can detect the second light beam regularly reflected by said face corresponding to the second plurality of incident angles;
a total reflection break angle obtaining unit for obtaining a total reflection break angle of the first light beam based on a result of detection by the light detecting unit; and
a Brewster's angle obtaining unit for obtaining a Brewster's angle of the second light beam based on a result of detection by the light detecting unit.

9. A surface plasmon sensor comprising:
a dielectric material;
a metal film formed on a face of the dielectric material and in contact with a sample;
a light source for generating a first light beam and a second light beam;
a first optical system for letting the first light beam pass through the dielectric material and letting the first light beam be incident on a boundary surface between the dielectric material and the metal film at a first plurality of incident angles;
a first light detecting unit which can detect the first light beam totally reflected by the boundary surface corresponding to the first plurality of incident angles;
a second optical system for letting the second light beam pass through the dielectric material and letting the second light beam be incident on said face of the dielectric material at a second plurality of incident angles;
a second light detecting unit which can detect the second light beam regularly reflected by said face corresponding to the second plurality of incident angles;
a total reflection break angle obtaining unit for obtaining a total reflection break angle of the first light beam based on a result of detection by the first light detecting unit; and
a Brewster's angle obtaining unit for obtaining a Brewster's angle of the second light beam based on a result of detection by the second light detecting unit.

10. A surface plasmon sensor comprising:
a dielectric material;
a metal film formed on a face of the dielectric material and in contact with a sample;
a first light source for generating a first light beam;
a second light source for generating a second light beam;
an optical system for letting the first light beam pass through the dielectric material and letting the first light beam be incident on a boundary surface between the dielectric material and the metal film at a first plurality of incident angles, and for letting the second light beam pass through the dielectric material and letting the second light beam be incident on said face of the dielectric material at a second plurality of incident angles;
a first light detecting unit which can detect the first light beam totally reflected by the boundary surface corresponding to the first plurality of incident angles;
a second light detecting unit which can detect the second light beam regularly reflected by said face corresponding to the second plurality of incident angles;
a total reflection break angle obtaining unit for obtaining a total reflection break angle of the first light beam based on a result of detection by the first light detecting unit; and
a Brewster's angle obtaining unit for obtaining a Brewster's angle of the second light beam based on a result of detection by the second light detecting unit.

11. A surface plasmon sensor comprising:
a dielectric material;
a metal film formed on a face of the dielectric material and in contact with a sample;
a light source for generating a light beam;
an optical system for letting the light beam pass through the dielectric material and letting the light beam be incident on a boundary surface between the dielectric material and the metal film at a first plurality of incident angles and letting the light beam be incident on said face of the dielectric material at a second plurality of incident angles;
a first light detecting unit which can detect the light beam totally reflected by the boundary surface corresponding to the first plurality of incident angles;
a second light detecting unit which can detect the light beam regularly reflected by said face corresponding to the second plurality of incident angles;
a total reflection break angle obtaining unit for obtaining a total reflection break angle of the light beam based on a result of detection by the first light detecting unit; and
a critical angle obtaining unit for obtaining a critical angle of the light beam based on a result of detection by the second light detecting unit.

12. A surface plasmon sensor comprising:
a dielectric material;
a metal film formed on a face of the dielectric material and in contact with a sample;
a light source for generating a light beam;
an optical system for letting the light beam pass through the dielectric material and letting the light beam be incident on a boundary surface between the dielectric material and the metal film at a first plurality of incident angles and letting the light beam be incident on said face of the dielectric material at a second plurality of incident angles;
a light detecting unit which can detect the light beam totally reflected by the boundary surface corresponding to the first plurality of incident angles and can detect the light beam regularly reflected by said face corresponding to the second plurality of incident angles;
a total reflection break angle obtaining unit for obtaining a total reflection break angle of the light beam based on a result of detection by the light detecting unit; and
a critical angle obtaining unit for obtaining a critical angle of the light beam based on a result of detection by the light detecting unit.

13. A surface plasmon sensor comprising:

a dielectric material;

a metal film formed on a face of the dielectric material and in contact with a sample;

a first light source for generating a first light beam;

a first optical system for letting the first light beam pass through the dielectric material and letting the first light beam be incident on a boundary surface between the dielectric material and the metal film at a first plurality of incident angles;

a second light source for generating a second light beam;

a second optical system for letting the second light beam pass through the dielectric material and letting the second light beam be incident on said face of the dielectric material at a second plurality of incident angles;

a light detecting unit which can detect the light beam totally reflected by the boundary surface corresponding to the first plurality of incident angles and can detect the light beam regularly reflected by said face corresponding to the second plurality of incident angles;

a total reflection break angle obtaining unit for obtaining a total reflection break angle of the first light beam based on a result of detection by the first light detecting unit;

a critical angle obtaining unit for obtaining a critical angle of the second light beam based on a result of detection by the second light detecting unit; and a unit for obtaining a difference between said total reflection break angle and said critical angle.

14. A surface plasmon sensor comprising:

a dielectric material;

a metal film formed on a face of the dielectric material and in contact with a sample;

a light source for generating a first light beam and a second light beam;

a first optical system for letting the first light beam pass through the dielectric material and letting the first light beam be incident on a boundary surface between the dielectric material and the metal film at a first plurality of incident angles;

a first light detecting unit which can detect the first light beam totally reflected by the boundary surface corresponding to the first plurality of incident angles;

a second optical system for letting the second light beam pass through the dielectric material and letting the second light beam be incident on said face of the dielectric material at a second plurality of incident angles;

a second light detecting unit which can detect the light beam regularly reflected by said face corresponding to the second plurality of incident angles;

a total reflection break angle obtaining unit for obtaining a total reflection break angle of the first light beam based on a result of detection by the first light detecting unit;

a critical angle obtaining unit for obtaining a critical angle of the second light beam based on a result of detection by the second light detecting unit; and a unit for obtaining a difference between said total reflection break angle and said critical angle.

15. A surface plasmon sensor comprising:

a dielectric material;

a metal film formed on a face of the dielectric material and in contact with a sample;

a first light source for generating a first light beam;

a second light source for generating a second light beam;

an optical system for letting the first light beam pass through the dielectric material and letting the first light beam be incident on a boundary surface between the dielectric material and the metal film at a first plurality of incident angles and letting the second light beam pass through the dielectric material and letting the second light beam be incident on said face of the dielectric material at a second plurality of incident angles;

a first light detecting unit which can detect the first light beam totally reflected by the boundary surface corresponding to the first plurality of incident angles;

a second light detecting unit which can detect the second light beam regularly reflected by said face corresponding to the second plurality of incident angles;

a total reflection break angle obtaining unit for obtaining a total reflection break angle of the first light beam based on a result of detection by the first light detecting unit;

a critical angle obtaining unit for obtaining a critical angle of the second light beam based on a result of detection by the second light detecting unit; and a unit for obtaining a difference between said total reflection break angle and said critical angle.

16. A surface plasmon sensor comprising:

a dielectric material;

a metal film formed on a face of the dielectric material and in contact with a sample;

a light source for generating a light beam;

an optical system for letting the light beam pass through the dielectric material and letting the light beam be incident on a boundary surface between the dielectric material and the metal film at a first plurality of incident angles and letting the light beam pass through the dielectric material and letting the light beam be incident on said face of the dielectric material at a second plurality of incident angles;

a first light detecting unit which can detect the light beam totally reflected by the boundary surface corresponding to the first plurality of incident angles;

a second light detecting unit which can detect the light beam regularly reflected by said face corresponding to the second plurality of incident angles;

a total reflection break angle obtaining unit for obtaining a total reflection break angle of the light beam based on a result of detection by the first light detecting unit;

a critical angle obtaining unit for obtaining a critical angle of the light beam based on a result of detection by the second light detecting unit; and a unit for obtaining a difference between said total reflection break angle and said critical angle.

17. A surface plasmon sensor comprising:

a dielectric material;

a metal film formed on a face of the dielectric material and in contact with a sample;

a light source for generating a light beam;

an optical system for letting the light beam pass through the dielectric material and letting the light beam be incident on a boundary surface between the dielectric material and the metal film at a first plurality of incident angles and letting the light beam be incident on said face of the dielectric material at a second plurality of incident angles;

a light detecting unit which can detect the light beam totally reflected by the boundary surface corresponding to the first plurality of incident angles and can detect the light beam regularly reflected by said face corresponding to the second plurality of incident angles;

a total reflection break angle obtaining unit for obtaining a total reflection break angle of the light beam based on a result of detection by the light detecting unit;

a critical angle obtaining unit for obtaining a critical angle of the light beam based on a result of detection by the light detecting unit; and a unit for obtaining a difference between said total reflection break angle and said critical angle.

18. A surface plasmon sensor comprising:

a dielectric material;

a metal film formed on a face of the dielectric material and in contact with a sample;

a light source for generating a light beam;

an optical system for letting the light beam pass through the dielectric material and letting the light beam be incident on a boundary surface between the dielectric material and the metal film at a first plurality of incident angles and letting the light beam be incident on said face of the dielectric material at a second plurality of incident angles;

a first light detecting unit which can detect the light beam totally reflected by the boundary surface corresponding to the first plurality of incident angles;

a second light detecting unit which can detect the light beam regularly reflected by said face corresponding to the second plurality of incident angles;

a total reflection break angle obtaining unit for obtaining a total reflection break angle of the light beam based on a result of detection by the first light detecting unit; and a Brewster's angle obtaining unit for obtaining a Brewster's angle of the light beam based on a result of detection by the second light detecting unit.

19. A surface plasmon sensor comprising:

a dielectric material;

a metal film formed on a face of the dielectric material and in contact with a sample;

a light source for generating a light beam;

an optical system for letting the light beam pass through the dielectric material and letting the light beam be incident on a boundary surface between the dielectric material and the metal film at a first plurality of incident angles and letting the light beam be incident on said face of the dielectric material at a second plurality of incident angles;

a light detecting unit which can detect the light beam totally reflected by the boundary surface corresponding to the first plurality of incident angles and can detect the light beam regularly reflected by said face corresponding to the second plurality of incident angles;

a total reflection break angle obtaining unit for obtaining a total reflection break angle of the light beam based on a result of detection by the light detecting unit; and a Brewster's angle obtaining unit for obtaining a Brewster's angle of the light beam based on a result of detection by the light detecting unit.

20. A surface plasmon sensor comprising:

a dielectric material;

a metal film formed on a face of the dielectric material and in contact with a sample;

a first light source for generating a first light beam;

a first optical system for letting the first light beam pass through the dielectric material and letting the first light beam be incident on a boundary surface between the dielectric material and the metal film at a first plurality of incident angles;

a second light source for generating a second light beam;

a second optical system for letting the second light beam pass through the dielectric material and letting the second light beam be incident on said face of the dielectric material at a second plurality of incident angles;

a light detecting unit which can detect the first light beam totally reflected by the boundary surface corresponding to the first plurality of incident angles and can detect the second light beam regularly reflected by said face corresponding to the second plurality of incident angles;

a total reflection break angle obtaining unit for obtaining a total reflection break angle of the first light beam based on a result of detection by the light detecting unit;

a Brewster's angle obtaining unit for obtaining a Brewster's angle of the second light beam based on a result of detection by the light detecting unit; and a unit for obtaining a difference between said total reflection break angle and said Brewster's angle.

21. A surface plasmon sensor comprising:

a dielectric material;

a metal film formed on a face of the dielectric material and in contact with a sample;

a light source for generating a first light beam and a second light beam;

a first optical system for letting the first light beam pass through the dielectric material and letting the first light beam be incident on a boundary surface between the dielectric material and the metal film at a first plurality of incident angles;

a first light detecting unit which can detect the first light beam totally reflected by the boundary surface corresponding to the first plurality of incident angles;

a second optical system for letting the second light beam pass through the dielectric material and letting the second light beam be incident on said face of the dielectric material at a second plurality of incident angles;

a second light detecting unit which can detect the second light beam regularly reflected by said face corresponding to the second plurality of incident angles;

a total reflection break angle obtaining unit for obtaining a total reflection break angle of the first light beam based on a result of detection by the first light detecting unit;

a Brewster's angle obtaining unit for obtaining a Brewster's angle of the second light beam based on a result of detection by the second light detecting unit; and a unit for obtaining a difference between said total reflection break angle and said Brewster's angle.

22. A surface plasmon sensor comprising:

a dielectric material;

a metal film formed on a face of the dielectric material and in contact with a sample;

a first light source for generating a first light beam;

a second light source for generating a second light beam;

an optical system for letting the first light beam pass through the dielectric material and letting the first light beam be incident on a boundary surface between the dielectric material and the metal film at a first plurality of incident angles and letting the second light beam pass through the dielectric material and letting the second light beam be incident on said face of the dielectric material at a second plurality of incident angles;

a first light detecting unit which can detect the first light beam totally reflected by the boundary surface corresponding to the first plurality of incident angles;

a second light detecting unit which can detect the second light beam regularly reflected by said face corresponding to the second plurality of incident angles;

a total reflection break angle obtaining unit for obtaining a total reflection break angle of the first light beam based on a result of detection by the first light detecting unit;

a Brewster's angle obtaining unit for obtaining a Brewster's angle of the second light beam based on a result of detection by the second light detecting unit; and a unit for obtaining a difference between said total reflection break angle and said Brewster's angle.

23. A surface plasmon sensor comprising:

a dielectric material;

a metal film formed on a face of the dielectric material and in contact with a sample;

a light source for generating a light beam;

an optical system for letting the light beam pass through the dielectric material and letting the light beam be incident on a boundary surface between the dielectric material and the metal film at a first plurality of incident angles and letting the light beam pass through the dielectric material and letting the light beam be incident on said face of the dielectric material at a second plurality of incident angles;

a first light detecting unit which can detect the light beam totally reflected by the boundary surface corresponding to the first plurality of incident angles;

a second light detecting unit which can detect the light beam regularly reflected by said face corresponding to the second plurality of incident angles;

a total reflection break angle obtaining unit for obtaining a total reflection break angle of the light beam based on a result of detection by the first light detecting unit;

a Brewster's angle obtaining unit for obtaining a Brewster's angle of the light beam based on a result of detection by the second light detecting unit; and a unit for obtaining a difference between said total reflection break angle and said Brewster's angle.

24. A surface plasmon sensor comprising:

a dielectric material;

a metal film formed on a face of the dielectric material and in contact with a sample;

a light source for generating a light beam;

an optical system for letting the light beam pass through the dielectric material and letting the light beam be incident on a boundary surface between the dielectric material and the metal film at a first plurality of incident angles and letting the light beam pass through the dielectric material and letting the light beam be incident on said face of the dielectric material at a second plurality of incident angles;

a light detecting unit which can detect the light beam totally reflected by the boundary surface corresponding to the first plurality of incident angles and can detect the light beam regularly reflected by said face corresponding to the second plurality of incident angles;

a total reflection break angle obtaining unit for obtaining a total reflection break angle of the light beam based on a result of detection by the light detecting unit;

a Brewster's angle obtaining unit for obtaining a Brewster's angle of the light beam based on a result of detection by the light detecting unit; and a unit for obtaining a difference between said total reflection break angle and said Brewster's angle.

* * * * *